United States Patent [19]

Mallory et al.

[11] Patent Number: 4,944,759
[45] Date of Patent: * Jul. 31, 1990

[54] POROUS-COATED ARTIFICIAL JOINTS

[75] Inventors: Thomas H. Mallory, Columbus; Timothy McTighe, Chagrin Falls, both of Ohio; Douglas G. Noiles, New Canaan, Conn.

[73] Assignee: Joint Medical Products Corporation, Stamford, Conn.

[*] Notice: The portion of the term of this patent subsequent to Nov. 28, 2006 has been disclaimed.

[21] Appl. No.: 402,803

[22] Filed: Sep. 5, 1989

Related U.S. Application Data

[63] Continuation of Ser. No. 256,126, Oct. 6, 1988, Pat. No. 4,883,491, which is a continuation of Ser. No. 820,772, Jan. 21, 1986, abandoned.

[51] Int. Cl.$^5$ ............... A61F 2/28; A61F 2/30; A61F 2/34
[52] U.S. Cl. ................. 623/22; 623/16; 623/18; 623/23
[58] Field of Search ............ 623/23, 22, 18, 17, 623/16

[56] References Cited

U.S. PATENT DOCUMENTS 3,840,904 11/1974 Tronzo .
4,038,703 8/1977 Bokros ............... 623/18 X
4,262,369 4/1981 Roux .
4,549,319 10/1985 Meyer ............... 623/18 X
4,550,448 11/1985 Kenna .
4,608,053 8/1986 Keller ............... 623/23
4,645,506 2/1987 Link ............... 623/23
4,662,891 5/1987 Noiles .
4,698,063 10/1987 Link et al. ............... 623/23

FOREIGN PATENT DOCUMENTS 65482 11/1982 European Pat. Off. .
179736 4/1986 European Pat. Off. .
2645101 4/1978 Fed. Rep. of Germany ........ 623/22
8431422 11/1985 Fed. Rep. of Germany .
3602081 10/1986 Fed. Rep. of Germany ........ 623/22
2554342 5/1985 France ............... 623/22
83/02555 8/1983 World Int. Prop. O. .

OTHER PUBLICATIONS

Sivash, K. M., *Alloplasty of the Hip Joint*, 1967, pp. 68–75, (original Russian article and translation).

Primary Examiner—Alan W. Cannon
Attorney, Agent, or Firm—Maurice M. Klee

[57] ABSTRACT

Artificial joint prostheses are provided whose outer surfaces include a screw thread which is interrupted by porous-coated columns so as to produce an alternating pattern of threaded columns adjacent to porous-coated columns. The threaded columns provide initial mechanical fixation of the prosthesis to bone and the porous-coated columns provide long-term fixation through bone ingrowth.

11 Claims, 2 Drawing Sheets

POROUS-COATED ARTIFICIAL JOINTS

This application is a continuation application of co-pending application Ser. No. 256,126 filed Oct. 6, 1988, now U.S. Pat. No. 4,883,491 which is a continuation of application Ser. No. 820,772, filed Jan. 21, 1986, now abandoned.

BACKGROUND OF THE INVENTION

1. Field of the Invention

This invention relates to artificial joints for implantation in the body and in particular to porous-coated artificial joints.

2. Description of the Prior Art

One of the critical problems in the field of artificial joints involves achieving a strong attachment between the patient's bone and the prosthesis both at the time of implantation and throughout the life of the prosthesis. A variety of approaches have been considered to solve this problem. For example, bone cement has been widely used to affix prostheses to bone. This approach in general provides a strong initial bond, but it has been found that the cement is often the first part of the prosthetic reconstruction to fail during use.

Mechanical fixation approaches have also been used. For example, the outside surfaces of prostheses have been provided with projections of various shapes designed to mechanically engage the patient's bone. Similarly, the outside surfaces of prostheses have been threaded, and the prosthesis screwed into the patient's bone to provide the desired mechanical fixation. Bone screws which pass through the prosthesis have also been used to provide fixation. These approaches frequently provide strong initial fixations which endure. However, some such apparently strong initial fixations become loose in time periods varying from a few weeks to a number of years. The reasons for such loosening are not known with certainty. The loosening, however, is an area in which such initially firm mechanical fixations clearly need to be improved.

Improved long-term fixation has been achieved through the use of porous-coated prostheses. In accordance with this approach, all or a part of the outside surface of the prosthesis is coated with small metal balls so as to produce a lattice work of submillimeter-sized interstices into which bone can grow. The bone ingrowth provides the desired long-term fixation. Unfortunately, in some situations, porous-coated prostheses lack good initial fixation.

In an attempt to provide both long-term and initial fixation, prostheses have been designed which incorporate both porous coating and mechanical fixation. Thus, an acetabular cup has been designed by Biomet, Inc., (Warsaw, Indiana), which includes a porous-coated dome and a circumferential, external thread located in the region adjacent the base (widest part or equator) of the cup. Also, Zimmer, Inc., (Warsaw, Indiana), Osteonics Corp. (Allendale, New Jersey), and others have made femoral components for hip prostheses which include 1) smooth, non-porous-coated portions sized to provide a mechanical, interference fit with a shaped cavity formed by the surgeon in the patient's bone, and 2) selected areas of porous coating.

Problems, however, have still remained. For example, the prostheses designed to date have only had limited porous-coated areas, e.g., only the dome of the prosthesis for the Biomet acetabular cup discussed above. Also, the porous-coated areas have been located in places where their effectiveness in providing strong fixation has been limited. Thus, in the case of acetabular cups, because of the anatomy of the pelvis and the moment arms involved, the most effective area for fixation is that area adjacent the base of the cup. Yet, to date, to achieve strong initial fixation, the external thread has been applied to the region of the base of the cup and the porous-coating has been applied only to the less effective dome region.

In the case of femoral stem prostheses, as discussed above, combinations of porous-coated portions together with smooth portions designed to provide a force fit in a shaped cavity in the bone have been used. None of these devices has included the combination of 1) porous-coated areas for long term fixation by bone ingrowth, and 2) means whereby the device could cut its own cavity or partial cavity to achieve a precise, secure, immediate mechanical fixation of the device to the patient's bone.

In view of the foregoing, the full potential of porous-coating as a means to achieve long-term prosthesis stability has not been realized in the prior art.

SUMMARY OF THE INVENTION

In view of the foregoing state of the art, it is an object of the present invention to provide improved prostheses which provide a strong bond to bone both initially upon implantation and throughout the life of the prosthesis. More particularly, it is an object of the invention to provide prostheses which include both external threads for providing initial fixation and porous-coated regions for providing long-term fixation, the porous-coated regions being of a greater area and being located at mechanically more advantageous positions than prior art prostheses having threaded and porous-coated regions. It is a further object of the invention to provide such improvements in porous-coated prostheses without sacrificing the initial fixation benefits provided by the external threading of the prosthesis.

To achieve the foregoing and other objects, the invention provides a prosthesis comprising a body having an outside surface upon which is formed a screw thread for engagement with bone, the screw thread being interrupted by porous-coated columns so as to produce an alternating pattern of threaded columns adjacent to porous-coated columns.

In certain preferred embodiments, the outer surfaces of the porous-coated columns lie substantially in or just above the surface of revolution defined by the root of the screw thread so that the porous-coated columns come into contact with bone as the prosthesis is screwed into the bone. In other preferred embodiments of the invention, the porous-coated columns and the threaded columns have approximately equal areas. This combination has been found to produce initial fixations of substantial strength. In further preferred embodiments, the screw thread is a self-tapping screw thread.

In the case of acetabular cups, the porous-coated and threaded columns are preferably located in the region of the base of the cup where the areas of fixation have a favorable anatomic and mechanical location. Also, for acetabular cups it is preferred to continue to porous-coat the dome portion of the cup as in the prior art. In this way, the invention provides significantly greater porous-coated areas than were achieved in the prior art. For example, in the case of an externally threaded acetabular cup of typical dimensions, the use of porous-coated columns and threaded columns of equal areas in combination with a porous-coated dome, results in an increase in the porous-coated area of the prosthesis of approximately 150% in comparison with just dome coating.

In addition to the increased porous-coated area, by placing the porous-coated columns in the region of the base of the cup, the porous-coated regions span more of the cup and have a greater relative moment arm of fixation than that achieved with just dome coating. As a result, once bone ingrowth has occurred, the porous coatings of the prostheses of the present invention have a more favorable mechanical fixation than prior art prostheses and thus are less likely to be dislodged during use.

The accompanying drawings, which are incorporated in and constitute part of the specification, illustrate the preferred embodiments of the invention, and together with the description, serve to explain the principles of the invention.

DESCRIPTION OF THE PREFERRED EMBODIMENTS

Figure 1:
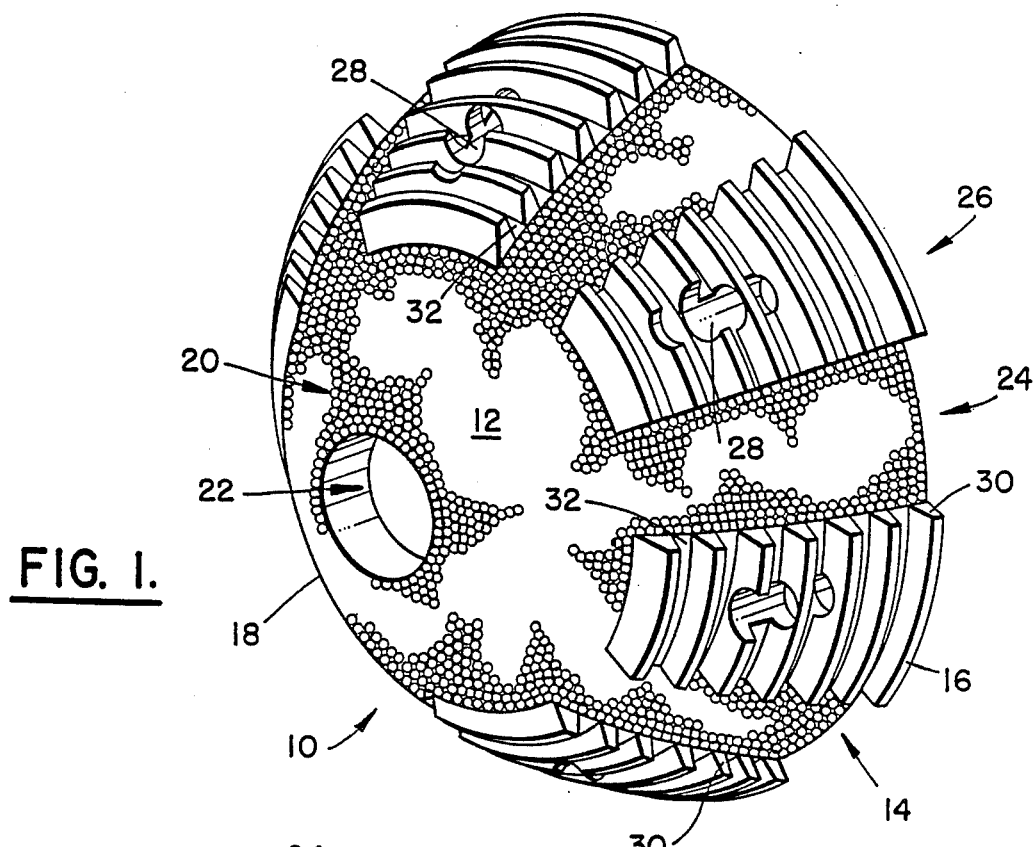
FIG. 1 is a perspective view of a porous-coated, threaded, acetabular cup constructed in accordance with the present invention.
Figure 2:
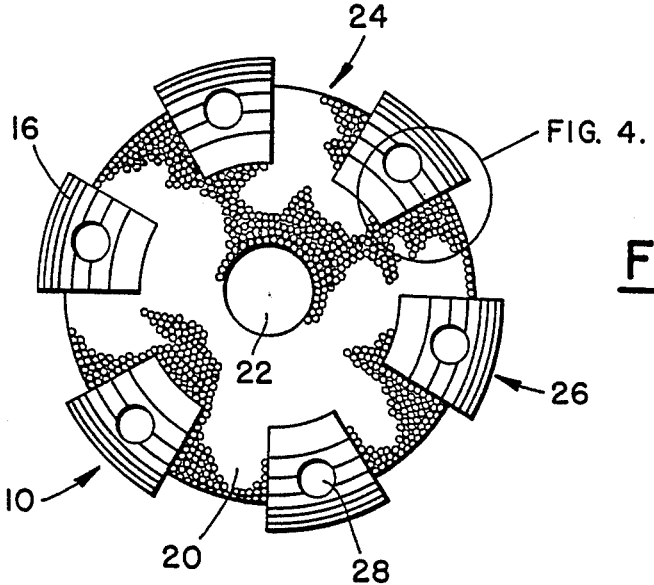
FIG. 2 is a top view of the cup of FIG. 1.
Figure 3:
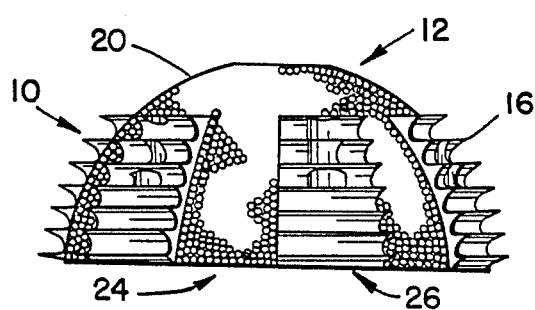
FIG. 3 is a side view of the cup of FIG. 1.
Figure 4:
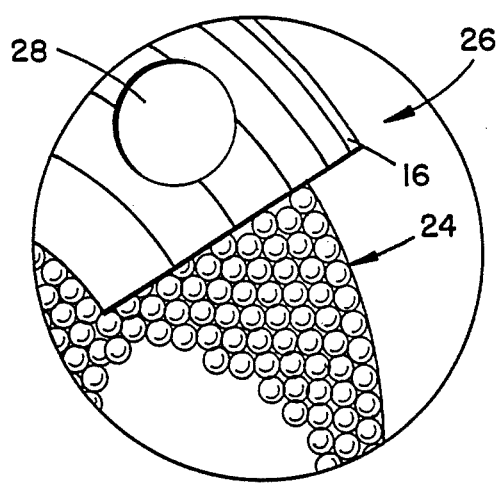
FIG. 4 is an enlarged view of the circled portion of FIG. 2.

Referring to the drawings, there is shown in FIGS. 1–4 a porous-coated, threaded acetabular cup 10 constructed in accordance with the present invention.

Cup 10 comprises body 18 having outer surface 20 which includes dome portion 12 and base portion 14. Surface 20 is preferably spherically-shaped. Body 18 preferably includes aperture 22 which extends from outer surface 20 through to the inside of the cup and allows the bone underlying the prosthesis to be viewed during the implantation process. Body 18 also preferably includes apertures 28 through which bone screws (not shown) can pass to further secure the prosthesis to the underlying bone, if desired. The bone screws can also be used to secure within body 18 a bearing insert (not shown) for receiving the ball portion of the artificial joint. Body 18 is preferably made of surgically implantable metal, and, in particular, is preferably made of a titanium alloy, such as an alloy containing 6% aluminum and 4% vanadium (see ASTM Spec. No. F136)

Thread 16 is formed on the outer surface of body 18 by, for example, casting or preferably by milling the surface using, for example, a computer-controlled machine tool. Preferably, thread 16 is a spherical thread, although a conical thread can be used, if desired. Also, thread 16 preferably includes leading edges 30 which are sufficiently sharp for the thread to be self-tapping. In practice, for an outer surface 20 having a diameter of between about 36 millimeters and about 72 millimeters, it has been found preferable to use a thread having a pitch of approximately 3 millimeters and a thread depth of approximately 3 millimeters. It has also been found preferable to have the bottom portion of surface 20 threaded so as to leave a non-threaded dome occupying a spherical segment whose base subtends a cone which has an apex at the center of the sphere and whose included cone angle is approximately 90°.

In accordance with the invention, the circumference of thread 16 is interrupted by a plurality of porous-coated columns 24, e.g., 3–12 columns, which divide the thread into an equal number of threaded columns 26. As shown in the figures, porous-coated columns 24 and threaded columns 26 alternate around the outer circumference of the prosthesis. Porous coated column areas 24 preferably lie on the same sphere as dome 12.

As also shown in the figures, porous-coated columns 24 and threaded columns 26 have approximately equal areas, although, if desired, the threaded columns can be given either a larger or smaller area than the porous-coated columns. Also, not all columns need have the same area, but rather large and small columns can be used on the same prosthesis, if desired. In general, porous-coated and threaded columns having approximately equal areas are preferred since this results in a secure level of initial fixation, and yet provides substantial porous-coated areas for long-term fixation through bone ingrowth. Preferably, in addition to porous-coated columns 24, dome portion 12 of outer surface 20 is also porous coated.

In practice, it has been found preferable to use a porous coating having an average pore size of between about 250 and about 350 microns, a porosity on the order of 39%, and a thickness of about one millimeter. It has also been found preferable to have the top surface of the porous coat lie substantially in the surface of revolution defined by roots 32 of thread 16 or slightly (e.g., 0.5 millimeters) above this surface. In this way, when the prosthesis has been screwed into bone, the porous coat will be in contact with bone and can thus accept bone ingrowth and remodeling. The top surface of the porous coat can be made to lie in the spherical surface defined by roots 32 by adjusting the depth of surface 20 in the area of columns 24 and dome 12 so that when the porous coat is applied, its top surface comes up to or slightly above the level of thread roots 32.

The porous coating can be applied to the outer surface of the prosthesis using various techniques known in the art. For example, columns 24 and dome 12 can be coated with small balls having a diameter of, for example, 0.4 to 0.7 millimeters, and the coated prosthesis can then be heated to fuse the balls to one another and to body 18. Preferably, the small balls used for porous coating will be made of an appropriate surgically implantable material such as chemically pure titanium or the titanium-aluminum-vanadium alloy described above. Porous coatings applied by plasma spray are also known in the art.

Once porous-coated and sterilized, acetabular cup 10 is implanted using known surgical procedures for implanting threaded acetabular cups. Thus, the patient's acetabulum is reamed using a spherical reamer having a diameter corresponding to the diameter of the spherical surface defined by the outer surface of porous coated columns 24 and dome 12. The cup is then threaded into the prepared cavity using an appropriate driver which engages the body of the cup. Since thread 16 is self-tapping, tapping of a thread into the walls of the prepared cavity prior to implantation of the cup is generally not necessary.

Figure 6:
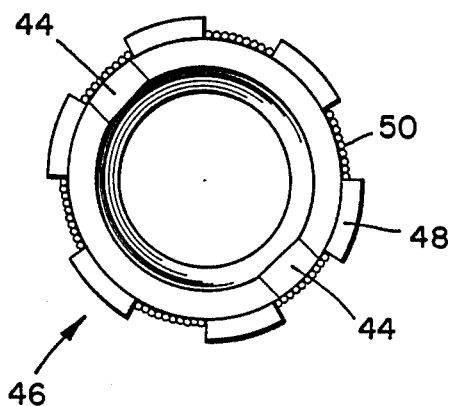
FIG. 6 is a top view of the sleeve of FIG. 5.
Figure 5:
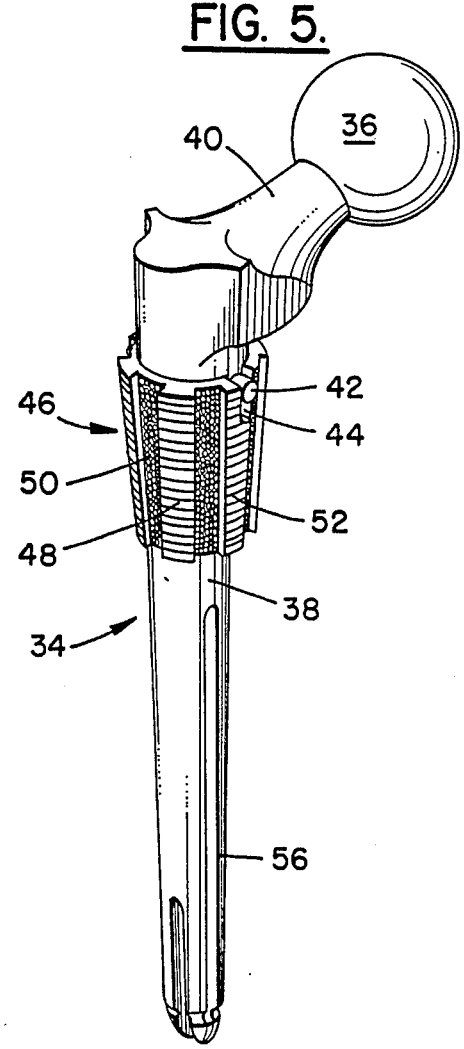
FIG. 5 is a perspective view of the femoral portion of an artificial hip joint employing a porous-coated, threaded sleeve constructed in accordance with the present invention.

Referring now to FIGS. 5-6, these figures illustrate the application of the principles of the present invention to the femoral portion of an artificial hip joint. In particular, there is shown in these figures a femoral prosthesis 34 comprising ball 36 which is connected to stem 38 by neck 40. Stem 38 mates with sleeve 46 by means of complementary locking tapers (not shown) on the outside of the stem and the inside of the sleeve. A pin 42 through stem 38 may be used to engage slots 44 of sleeve 46 to establish angular orientation of neck 40 relative to the femur bone in which sleeve 46 has been implanted. Torque and longitudinal forces between stem 38 and sleeve 46 are transmitted through the locking taper, however.

The prosthesis is implanted using standard surgical techniques by, for example, preparing the patient's femoral bone to receive the distal portion 56 of stem 38 and threading sleeve 46 into the prepared proximal femur, using an appropriate driving and aligning instrument which engages sleeve 46 by its internal taper and by slots 44. Lastly, stem 38 is driven into the complementary locking taper of sleeve 46.

In accordance with the invention, sleeve 46 includes threaded columns 48 and porous columns 50. As with the acetabular cup of FIGS. 1-4, threaded columns 48 provide initial, mechanical fixation of the prosthesis, while porous-coated columns 50 provide long-term fixation by means of bone ingrowth and remodeling. As discussed above in connection with the acetabular cup embodiment, porous-coated columns 50 preferably have approximately the same projected cylindrical area as threaded columns 48, and the top surface of the porous coat preferably lies in or near to the surface of revolution defined by the roots of threads 52.

Although specific embodiments of the invention have been described and illustrated, it is to be understood that modifications can be made without departing from the invention's spirit and scope. For example, the alternating porous-coated and threaded portions of the prosthesis can have configurations other than those illustrated in the figures. Similarly, the invention can be applied to prostheses other than an artificial hip joint as used for purposes of illustration in the figures, e.g., to artificial knee, shoulder and finger joints.

What is claimed is:

1. A prosthesis comprising a body having an outside surface upon which is formed a screw thread for engagement with bone, the screw thread being interrupted by porous-coated columns so as to produce an alternating pattern of threaded columns adjacent to porous-coated columns, the threaded columns being free of porous coating and providing initial mechanical fixation of the prosthesis to the bone and the porous-coated columns allowing long-term fixation through bone ingrowth and remodeling.

2. The prosthesis of claim 1 wherein the porous-coated columns and the threaded columns have approximately equal areas.

3. The prosthesis of claim 1 wherein the outer surfaces of the porous-coated columns lie substantially in or slightly above the surface of revolution defined by the root of the screw thread so that the porous-coated regions come into contact with bone as the prosthesis is screwed into the bone.

4. The prosthesis of claim 1 wherein the screw thread is self-tapping.

5. The prosthesis of claim 1 wherein the body comprises a cup for use as part of an artificial ball and socket joint and the porous-coated columns extend into the region of the base of the cup where the cup is of greatest width.

6. The prosthesis of claim 1 wherein the body comprises a sleeve for receiving a stem attached to the ball portion of an artificial ball and socket joint.

7. A prosthesis comprising a cup for use as part of an artificial ball and socket joint, said cup having an outside surface upon which is formed a screw thread for engagement with bone, said outside surface including a dome portion and a base portion, the base portion including (a) the screw thread and (b) a plurality of porous-coated columns which extend from the dome portion into the region of the base of the cup where the cup is of greatest width, said screw thread being free of porous coating and being interrupted by the porous-coated columns so as to produce an alternating pattern of threaded columns adjacent to porous-coated columns, the threaded columns providing initial mechanical fixation of the prosthesis to the bone and the porous-coated columns allowing long-term fixation through bone ingrowth and remodeling.

8. The prosthesis of claim 7 wherein the outside surface is spherically shaped.

9. The prosthesis of claim 7 wherein the porous-coated columns and the threaded columns have approximately equal areas.

10. The prosthesis of claim 7 wherein the outer surfaces of the porous-coated columns lie substantially in or slightly above the surface of revolution defined by the root of the screw thread so that the porous-coated regions come into contact with bone as the prosthesis is screwed into the bone.

11. The prosthesis of claim 7 wherein the screw thread is self-tapping.

* * * * *